(12) United States Patent
Makins (10) Patent No.: US 10,083,492 B2
(45) Date of Patent: Sep. 25, 2018

(54) METHOD AND SYSTEM FOR COLLABORATIVE LEARNING

(71) Applicant: Parish Episcopal School, Dallas, TX (US)

(72) Inventor: Jennifer Makins, Farmers Branch, TX (US)

(*) Notice: Subject to any disclaimer, the term of this patent is extended or adjusted under 35 U.S.C. 154(b) by 199 days.

(21) Appl. No.: 15/207,965

(22) Filed: Jul. 12, 2016

(65) Prior Publication Data
US 2017/0345110 A1 Nov. 30, 2017

Related U.S. Application Data (60) Provisional application No. 62/342,571, filed on May 27, 2016.

(51) Int. Cl.
| | |
|---|---|
| *G09B 7/00* | (2006.01) |
| *G06Q 50/22* | (2018.01) |
| *H04L 29/08* | (2006.01) |
| *H04L 29/06* | (2006.01) |
| *G09B 5/12* | (2006.01) |
| *G06F 19/00* | (2018.01) |
| *G06Q 10/10* | (2012.01) |
| *G09B 5/00* | (2006.01) |

(52) U.S. Cl.
CPC ............ *G06Q 50/22* (2013.01); *G06F 19/00* (2013.01); *G06Q 10/101* (2013.01); *G09B 5/00* (2013.01); *G09B 5/125* (2013.01); *H04L 63/083* (2013.01); *H04L 63/102* (2013.01); *H04L 67/02* (2013.01); *H04L 67/025* (2013.01); *H04L 63/168* (2013.01)

(58) Field of Classification Search
CPC ................................................ G09B 7/00
See application file for complete search history.

(56) References Cited

U.S. PATENT DOCUMENTS

| | | | |
|---|---|---|---|
| 7,480,597 B2 * | 1/2009 | Clark ............... | G06F 17/50 700/106 |
| 2004/0153509 A1 * | 8/2004 | Alcorn ............. | G06Q 30/06 709/205 |

OTHER PUBLICATIONS

Krishnan, Gokul, "Designing a Mobile Makerspace for Children's Hospital Patients: Enhancing Patients' Agency and Identity in Learning," Dissertation, Vanderbilt University, Dec. 2015.

* cited by examiner

*Primary Examiner* — Omkar Deodhar
(74) *Attorney, Agent, or Firm* — John J. Patti; Miller Patti Pershern PLLC (57) ABSTRACT

A method for educating a patient through a collaborative network is provided. The patient is authenticated with a username and a password. A request is received by a server for entry to a repository for educational design activities. Each of educational design activities includes exemplar design configurations and material lists and is configured to include photographs and written texts for other patients who have completed the associated educational design activity. A hypertext document is transmitted to the client computer—which includes the education design activities. The hypertext document is configured to be displayed through a browsing application on the client computer. A request is received by the server from the client computer for access to a selected education design activity, and access is provided to a design engine for the selected educational design activity. A design file created by the patient is then stored using the design engine.

16 Claims, 8 Drawing Sheets

METHOD AND SYSTEM FOR COLLABORATIVE LEARNING

CROSS-REFERENCE TO RELATED APPLICATIONS

This application claims priority to provisional U.S. Patent Application Ser. No. 62/342,571, entitled "Method and System for Collaborative Learning," filed on May 27, 2016, which is hereby incorporated by reference for all purposes.

TECHNICAL FIELD

The invention relates generally to a method and system for educating and, more particularly, to a collaborative system for educating child patients confined to a hospital.

BACKGROUND

Child illness (such as childhood cancers) can have a defining and significant impact on the well-being of the patients. This is not just limited to the physical health, but mental health as well. Children in these situations—who are usually bedridden and/or hospital bound—are typically isolated in that their daily interactions do not include the normal socialization with other children of the same age. This type of isolation can lead to a number of problems including depression and loss of education. This is not an entirely new problem; it is, in fact, quite well-known. And, there have been attempts to curb the problems—at least from an educational perspective.

Figure 1:
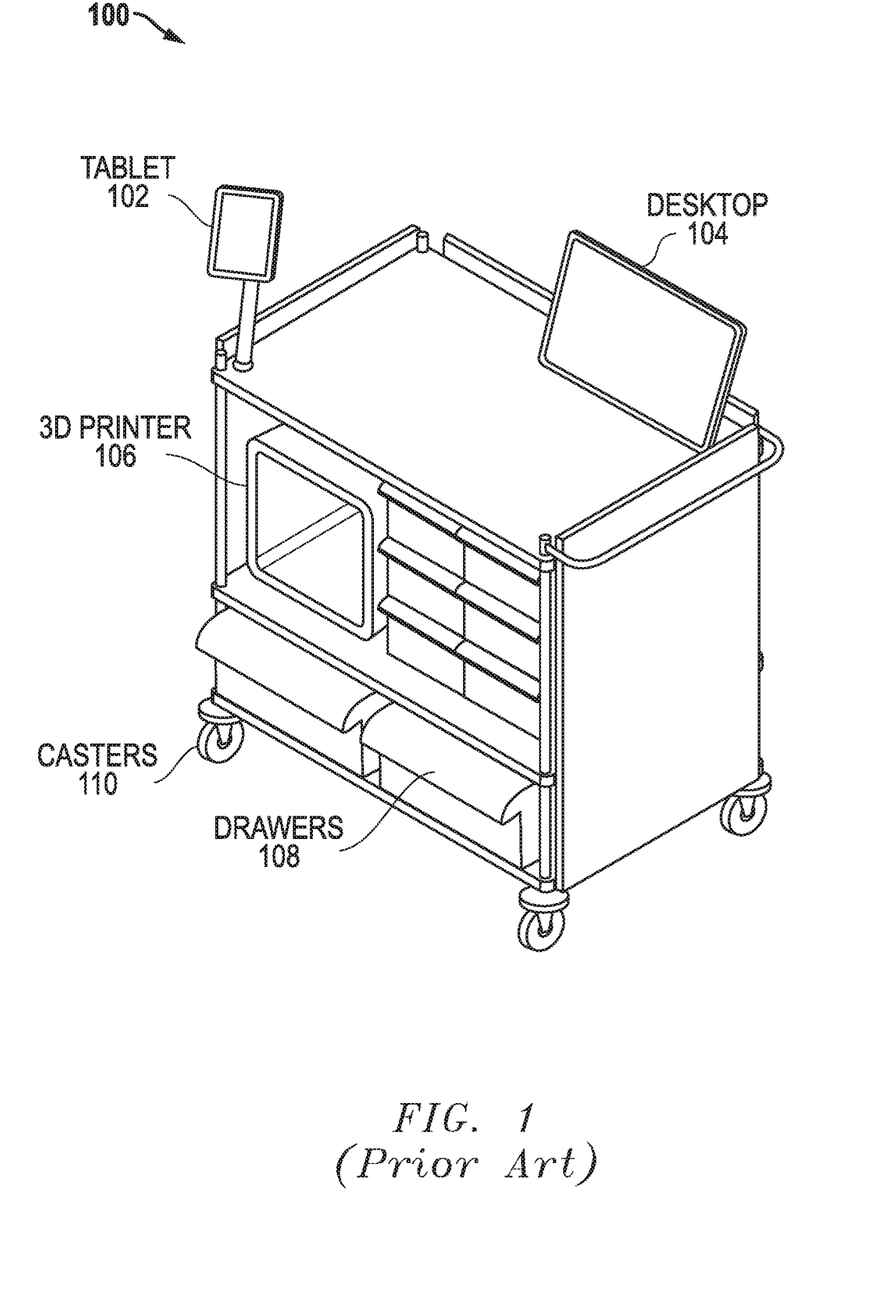
FIG. 1 is an example of a prior art cart shared workstation.

Probably the most significant development is a cart developed at Vanderbilt University—called "Makerspace." An example of the Makerspace 100 can be seen in FIG. 1. As shown, this cart 100 is a shared workstation. This cart is a mobile creation station—thanks to the casters 110—which includes two separate computers (i.e., a table 102 and desktop 104) which allows the children to gain access to educational materials. It also includes a three dimensional (3D) printer 106 and a number of drawers 108 for storage of education items (e.g., electronics). This allows the children full access to materials to help alleviate many of the educational boundaries imposed by hospitalization, and the totality of this system can be seen in the Dissertation of Gokul Krishnan, dated December 2015 from Vanderbilt University and hereby incorporated by reference.

While the Makerspace 100 is a step in the right direction, it remains incomplete. It does help hospital-bound children stay on the same educational curve as other healthy children, but it does not help alleviate any issues with socialization or isolation. Makerspace 100 is also lacking in that it does not provide any type of peer-based collaborative atmosphere to help motivate hospital-bound children.

Therefore, there is a need for a collaborative educational system and method to allow ill children to both socialized and learn.

SUMMARY

An embodiment of the present invention, accordingly, provides a method for educating a patient through a collaborative network. The method comprising: authenticating the patient with a username and a password, wherein the username and password are registered by way of an authentication number provided through a hospital entry process such that the authentication number ensures the authenticity of the patient and ensures that patient information is gapped to ensure privacy; receiving a request by a server from a client computer for entry to a repository for a plurality of educational design activities, wherein each of the plurality of educational design activities includes exemplar design configurations and material lists, and wherein each of the plurality of educational design activities is configured to include photographs and written texts for other patients who have completed the associated educational design activity; transmitting a hypertext document to the client computer that includes the plurality of education design activities, wherein the hypertext document is configured to be displayed through a browsing application on the client computer; receiving a request by the server from the client computer for access to a selected education design activity; providing access to a design engine for the selected educational design activity; and storing a design file created by the patient using the design engine.

In accordance with an embodiment of the present invention, the step of authenticating further comprises creating a secure socket layer (SSL) session.

In accordance with an embodiment of the present invention, the design engine is a computer aided design (CAD) engine is stored remotely from the client computer and accessed through the browsing application on the client computer.

In accordance with an embodiment of the present invention, the CAD file further comprise a plurality of CAD files.

In accordance with an embodiment of the present invention, the CAD engine is stored remotely from the client computer and accessed through the browsing application on the client computer.

In accordance with an embodiment of the present invention, wherein the design file further comprises a CAD file, and wherein the method further comprises: transmitting the design file to a shared workstation, wherein the shared workstation includes a vinyl cutting machine; and generating vinyl shapes based at least in part on the CAD file In accordance with an embodiment of the present invention, the design file further comprises a CAD file, and wherein the method further comprises: transmitting the design file to a shared workstation, wherein the shared workstation includes a three-dimensional (3D) printer; and printing a component on the 3D printer based at least in part on the CAD file.

In accordance with an embodiment of the present invention, the CAD file is stored remotely from the client computer.

In accordance with an embodiment of the present invention, the browsing application is a web browser.

In accordance with an embodiment of the present invention, the client computer is located on the shared workstation.

In accordance with an embodiment of the present invention, the client computer is a tablet.

In accordance with an embodiment of the present invention, the password associated with an authentication code the patient.

In accordance with an embodiment of the present invention, a system for collaboratively educating a patient is provided. The system comprising: a server that is adapted to serve a plurality of client computers, wherein each client computer is associated with at least one patient, wherein the server has a computer program product embodied thereon, and wherein the computer program includes: computer code for authenticating a first patient from the plurality of patients on a first client computer of the plurality of client computers with a first username and a password, wherein the username and password are registered by way of an authentication number provided through a hospital entry process such that the authentication number ensures the authenticity of the patient and that ensures that patient information is gapped to ensure privacy; computer code for receiving a request by the server from first client computer for entry to a repository for a plurality of educational design activities, wherein each of the plurality of educational design activities includes exemplar design configurations and material lists, and wherein each of the plurality of educational design activities is configured to include photographs and written texts for other patients who have completed the associated educational design activity; computer code for transmitting a hypertext document to the first client computer that includes the plurality of education design activities, wherein the hypertext document is configured to be displayed through a browsing application on the first client computer; computer code for receiving a request by the server from the first client computer for access to a selected education design activity; computer code for providing access to a design engine for the selected educational design activity; and computer code for storing a design file created by the first patient using the design engine; and a shared workstation that is configured to receive control instructions from the server, wherein the workstation includes a 3D printer that is configured to generate components in response to design data supplied by the server, wherein the design data includes the design file.

In accordance with an embodiment of the present invention, a method for educating a patient through a collaborative network is provided. The method comprising: receiving a request for access by an activity server over a switched packet network to a webpage from a web browser resident on a client computer associated with the patient; transmitting a first hypertext document to the client computer over the switched packet network, wherein the first hypertext document includes entry boxes for a username and password, and wherein the username and password are associated with an authentication number provided through a hospital entry process such that the authentication number ensures the authenticity of the patient and ensures that patient information is gapped to ensure privacy; authenticating the patient with the username and the password through the use of an authentication server so as to use an SSL session; transmitting a second hypertext document to the client computer, wherein the second hypertext document, when rendered on the web browser resident on the client computer, includes a banner with a plurality of selection buttons, wherein a first selection button from the plurality of selection includes permits access a repository for a plurality of education design activities; receiving a request by the activity server from the client computer for entry to the repository, wherein each of the plurality of educational design activities includes exemplar design configurations and material lists, and wherein each of the plurality of educational design activities is configured to include photographs and written texts for other patients who have completed the associated educational design activity; receiving a request by the server from the client computer for access to a selected education design activity; providing access to a CAD engine for the selected educational design activity, wherein the CAD engine operates remotely from the client computer, and wherein the CAD engine is configured to be manipulated through the web browser; and storing a design file created by the patient using the design engine at a location remote from the client computer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Refer now to the drawings wherein depicted elements are, for the sake of clarity, not necessarily shown to scale and wherein like or similar elements are designated by the same reference numeral through the several views.

Figure 2:
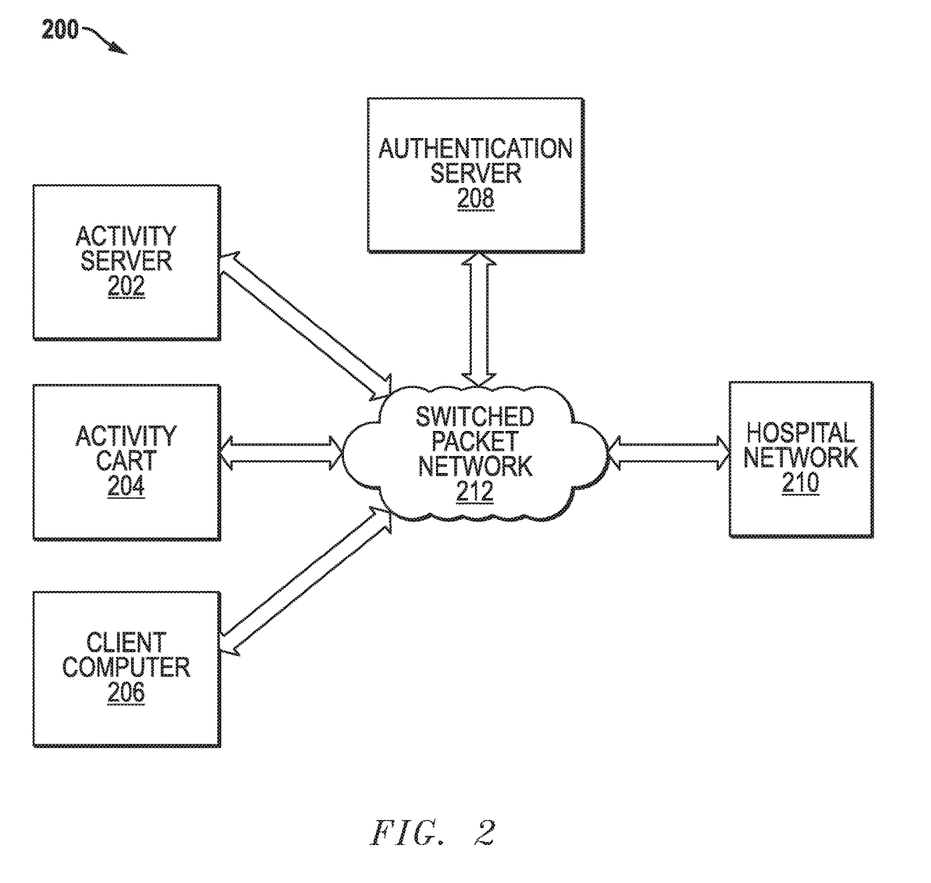
FIG. 2 is a block diagram of an example of a collaborative system in accordance with an embodiment of the present invention.

Referring to FIG. 2, a block diagram of an example of a collaborative education system 200 in accordance with an embodiment of the present invention can be seen. As shown, content for the collaborative system 200 is generally delivered by the activity server 202 (which may be comprised of multiple servers at one or various locations). Service of content (e.g., webpages and hypertext documents) is generally provided through well-known switched packet networks 212 (like the Internet). In operation, the client computer 206 makes requests for content from the activity server 202 over this switched packet network 212. For the sake of simplicity, only one client computer 206 is depicted, but there can be multiple client computers 206—which may be simultaneously served by server 202. Additionally, there may be an activity cart 204 (which is similar in structure and operation to the cart 100 of FIG. 1) may access the server 202 as well.

One particularly significant issue in a healthcare environment is privacy of patient data as required by statute. Essentially, the hospital generally needs to limit access to ensure that "authentic" patients have access to the educational system 200 while ensuring patient information is "gapped." In other words, the hospital network 210 uses the same switched packet network 212 to access the authentication server 202 so as to provide authentication numbers for authentic patients. That way, there is an association between the authentic patients and the usernames and passwords without direct access to patient information (e.g., separate databases)—"gapping" the patient information. An example operation 300 of this system 200 is then in FIG. 3 below with example page rendering shown in FIGS. 4-8.

Figure 3:
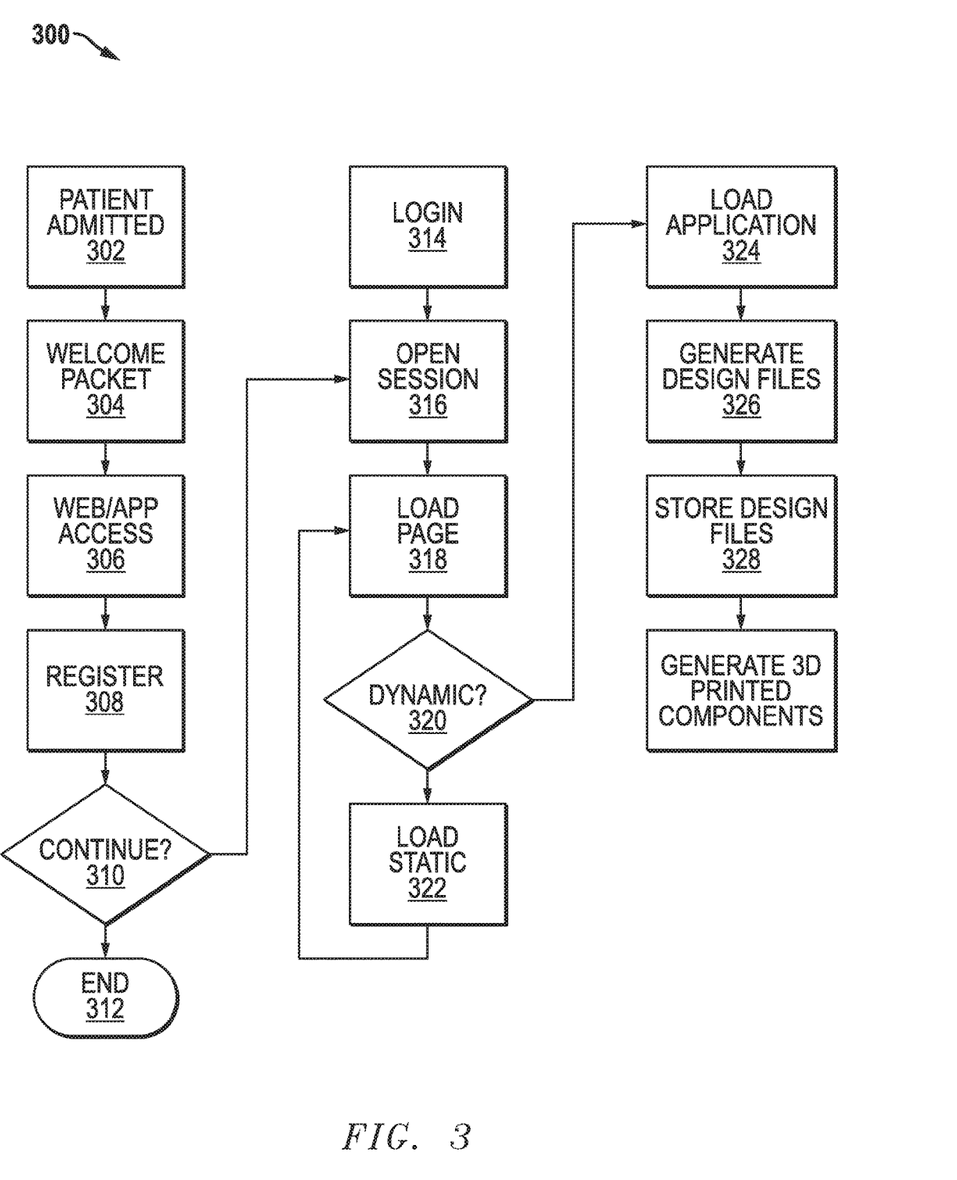
FIG. 3 is flow diagrams depicting an example operation of the system of FIG. 2.

Typically, when a patient is admitted to the hospital (step 302), the parent and patient receive a welcome packet and activity kit (step 304). These welcome materials include uniform resource locators (URLs) or web addresses for the collaborative site along with an authentication code. The authentication code can be generated by the hospital network 210 or included as part of kit materials provided to the hospital and is typically single use. Alternatively, an application may be provided for download to a mobile device (e.g., tablet or smartphone) instead of or in conjunction with a URL. Additionally, access to the network 200 can also be limited to IP addresses available from within the hospital to ensure integrity of the system 200 and for security reasons. Alternatively, parents of the child patients may be permitted access from IP address outside the hospital.

At the first access to the system 200 (either through a URL on a browser or through an app for example), the patient can create an account through registration (in steps 306 and 308). The patient will first enter the authentication code, and, once the authentication code is verified, the patient is prompted for a username and password—at which point the authentication code is destroyed. The username and password will then allow the patient to establish a session (step 316) with the network 200. Typically, the sessions are encrypted (again for security and privacy reason) using—for example—secure socket layer (SSL) sessions via OpenSSL and employing an authentication server 208. After the initial session, the patient can terminate the session (step 312) or continue on.

One advantage of the system 200 is that it is typically not resource limited. With prior cart systems (e.g., system 100), there was a single shared workstation—meaning that access to educational resources was limited in time so that many patients could not use it concurrently. With network 200, a patient may use his or her own equipment (client computer 206) for access and use the activity cart 204 when available. This means that a patient can simply access resources while the activity cart 204 is occupied.

When a patient opens an authentication session (step 316), a page 400-1 to 400-5 is rendered or loaded in step 318 for access to the content available from the activity server 202. Typically, this is accomplished through a web browser or app resident on the client computer 206 (e.g., child's tablet, smartphone, personal computer (PC), or laptop) making requests for access to content. Based on these requests from the browser or app, the server 202 typically provides hypertext documents (e.g., interactive graphical user interfaces) rendered in the browser or app. As shown in the example of FIGS. 4-8, there is a banner 402 located at the top of the rendered hypertext document that has various buttons such that the resident browser or app can request access to various content items.

Typically, there are two types of content that are accessed (in step 320): dynamic and static. Static content—which is loaded in step 322—generally constitutes basic web content like images, text, and video. Dynamic content—which is loaded in step 324—is active content; in other words, an application is either launched remotely and controller through the browser or app or is loaded locally—which interacts with the server 202. Examples of the types of applications include computer aided design (CAD) or electronic modeling (e.g., SPICE modeling software). Design files (e.g., CAD files) can then be generated from the launched application by the patient in step 326 and stored either locally or remotely in step 328. Once complete, the server 202 can transmit the design files (e.g., CAD files) to the 3D printer or vinyl slicer on the activity cart 204 to generate components.

Figure 4:
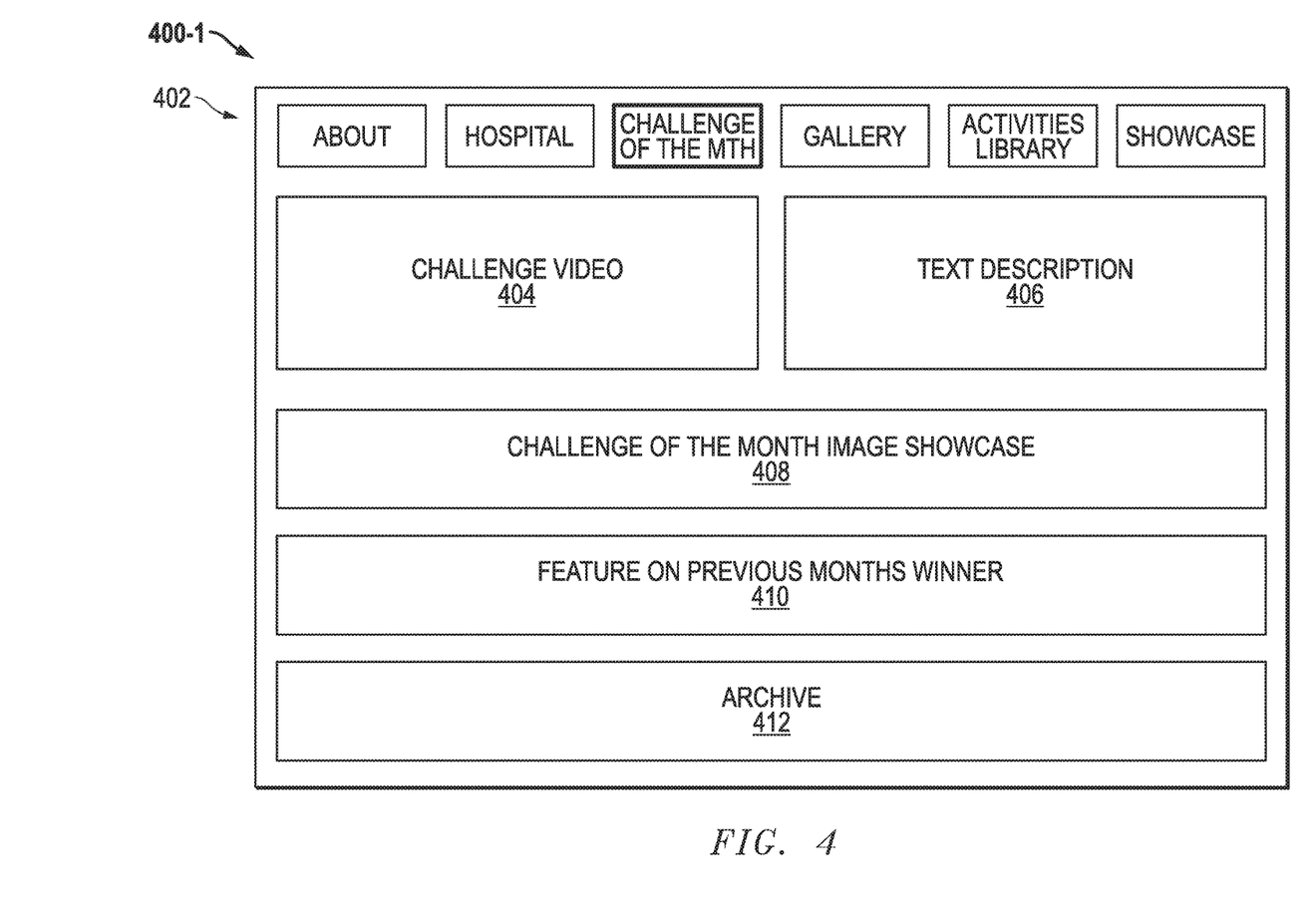
FIGS. 4-8 are block diagrams of rendered hypertext documents corresponding to the operation of the system of FIGS. 2 and 3.

Turning to FIG. 4, an example of a rendered hypertext document or page 400-1 can be seen. As shown, this page 400-1 include the banner 402—discussed above—with the "Challenge of the Month" button selected. This is accomplished by having the client computer 206 requests content from the server 202—which transmits the hypertext document to the client computer 206. As shown, this page 400-1 includes static content. Typically, the "Challenge of the Month" is a design competition created by the educators and issued to the patients. Considering that the system 200 is usually coupled to the Internet as its main switched packet network 212, the challenges can be amongst children of various networked hospitals. On this page 200-1, there is a video describing the challenge 404 and a textual description 406. An example of a challenge would be to design and build a Halloween-themed room decoration such as a nightlight for a nearby medical equipment pole. Images of others patients' in-progress and completed projects can be displayed in the showcase bar 408, and a feature discussing the previous month's winner can be found in bar 410. Archives of previous challenges can be though the archive bar 412 at the bottom of page 400-1.

Figure 5:
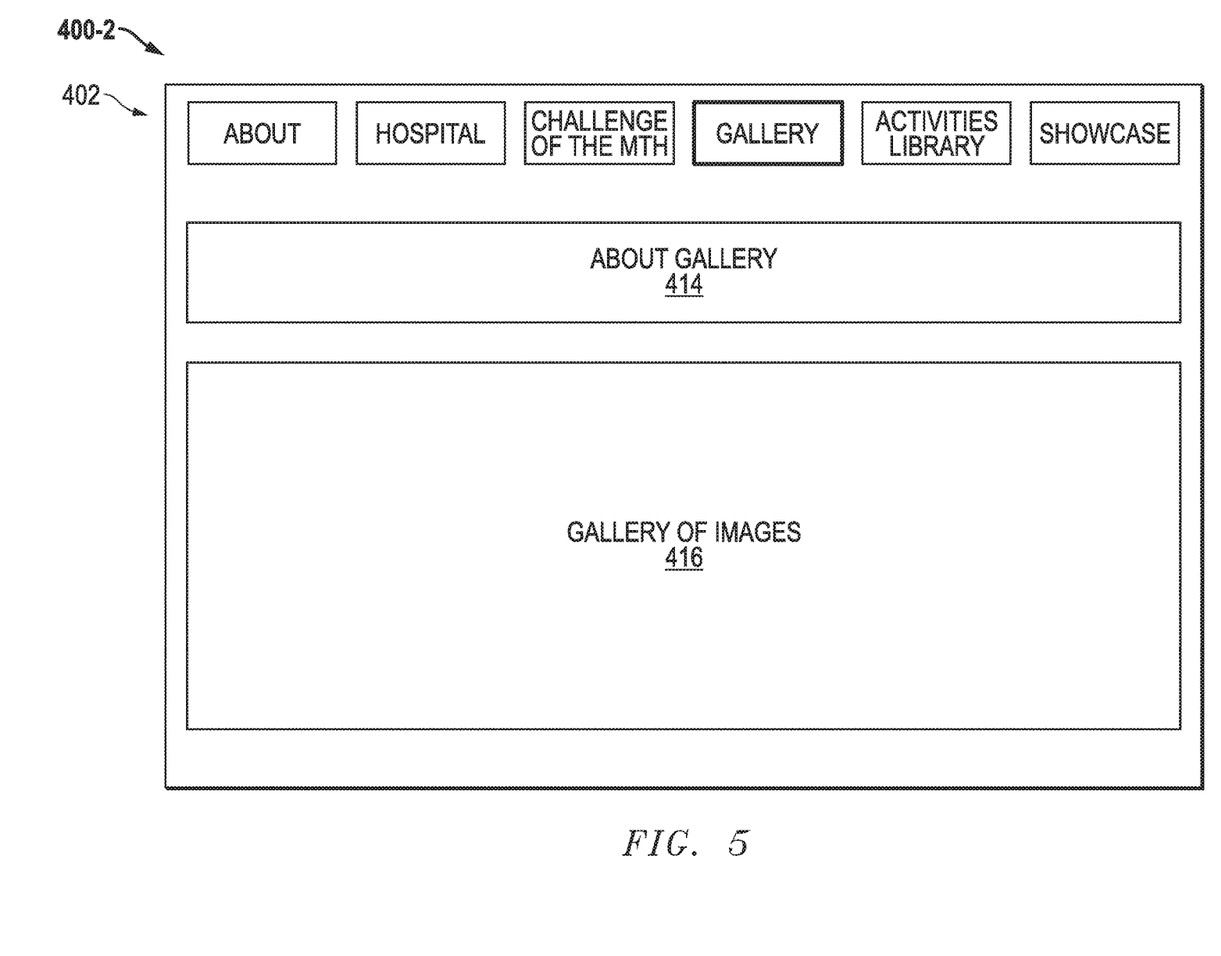

FIG. 5 shows an example of a rendered page 400-2 for the "Gallery." This "Gallery" is typically accessed through a request made through the banner 402 or through the archive bar 412 on page 400-1. Similar to page 400-1, this page 400-2 in this example, too, contains static content (e.g., images and text). Specifically, as shown in this example, there is a description banner 414 and the thumbnail gallery 416 of images of patients' projects and text.

Figure 6:
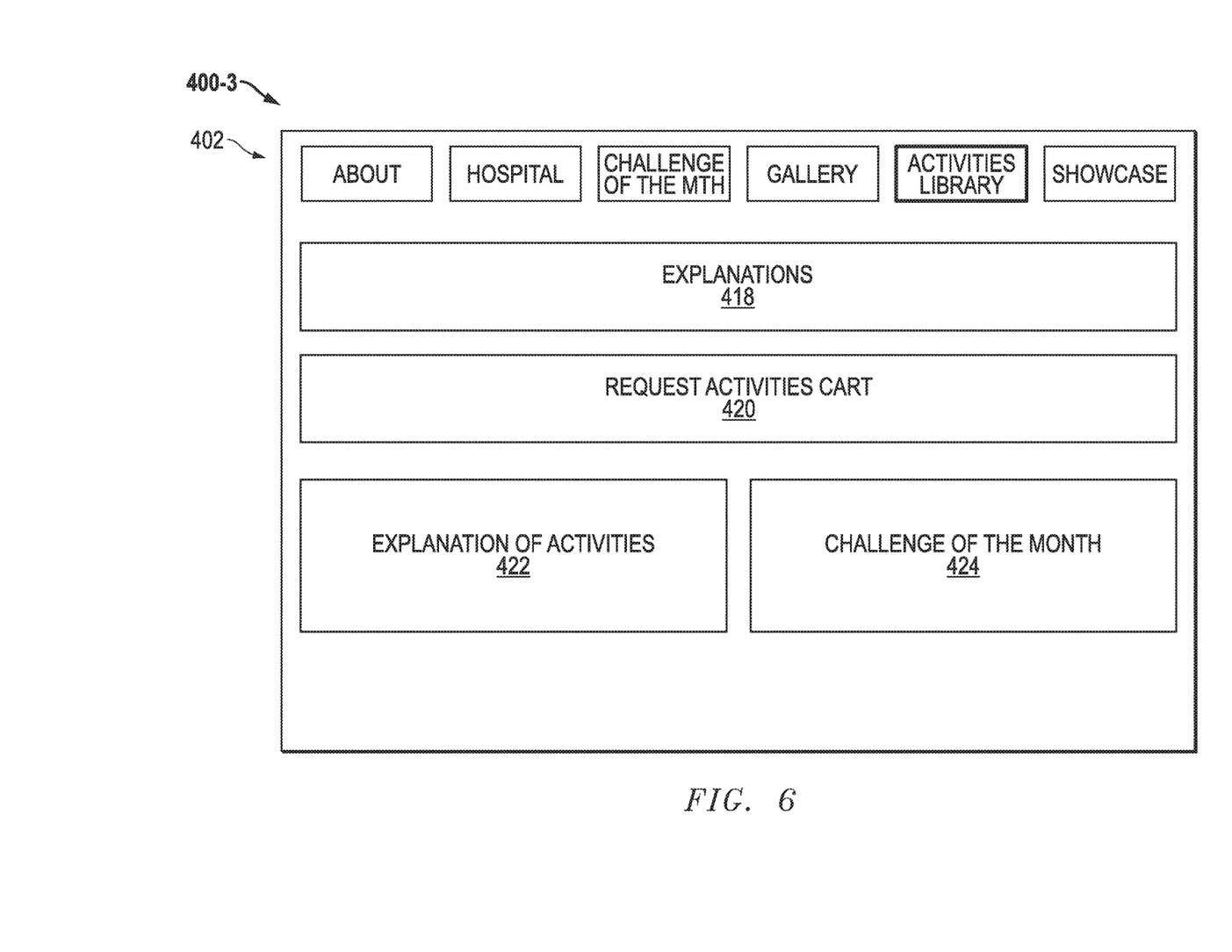
Figure 7:
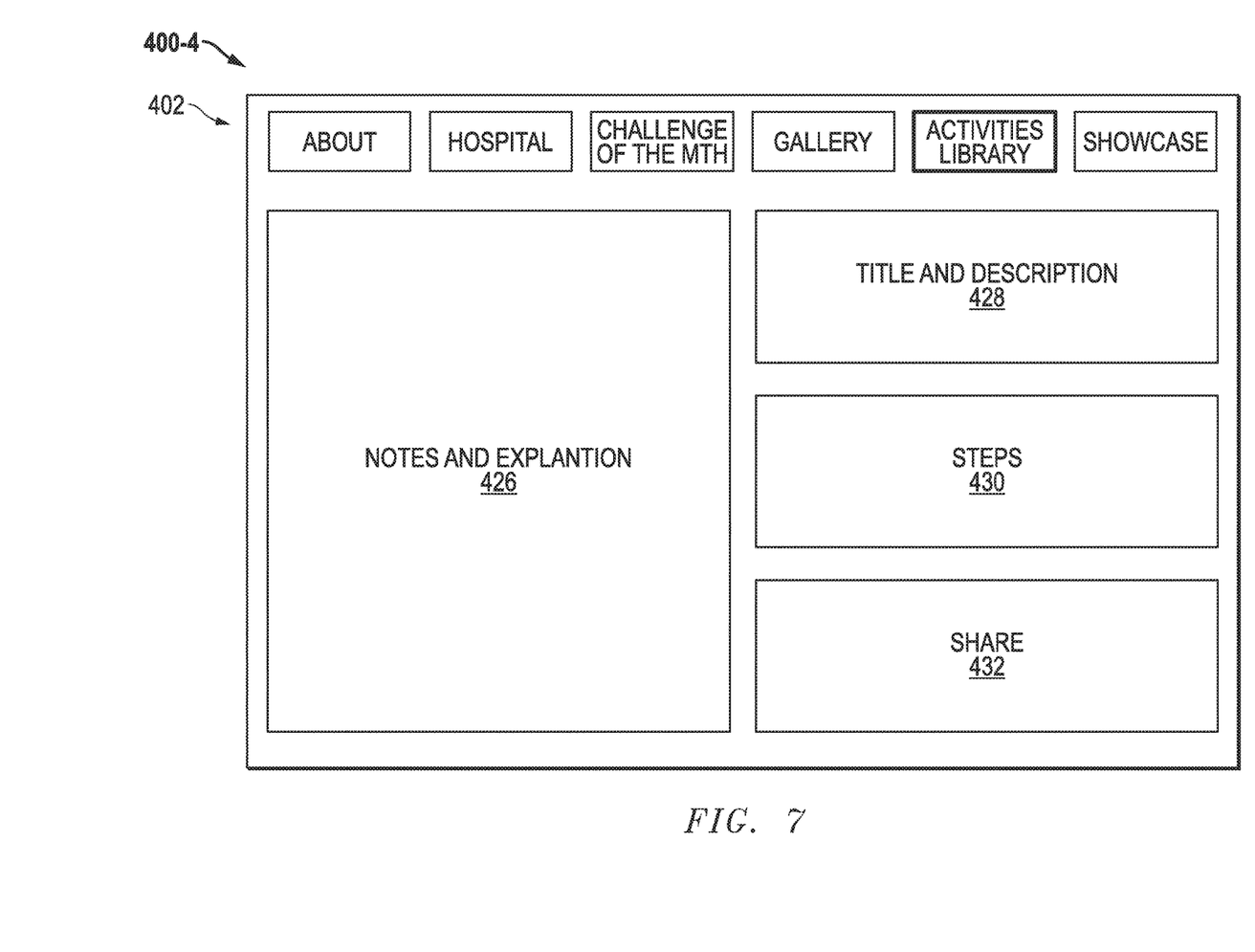

In FIGS. 6 and 7, there is an example of rendered page 400-3 and 400-4 for the "Activities Library." The "Activities Library" typically functions as a repository of design activities for the patients to attempt. Bar 418 serves as provide an overview of the page 400-3. Typically, there is a description of the kits for the various activities (which would usually include design components like electronics), lists of web application, and requirements to obtain the kits (e.g., completion of other challenges). Requests can also be made for the activity carts 204 in bar 420 where the patient can include information regarding the activity and kits needed to be supplied with the activity cart. Based on an activity selected in the explanations bar 418, an abbreviated explanation of what is involved is populated in the explanation of activity of activities bar 422. Typically, there is an explanation regarding the types of electronics, programming, experimentation, and CAD software that would be used for the activity. There is also typically access to the "Challenge of the Month" (page 400-1) in bar 424.

From the explanation of activities bar 422, the client computer 206 can request a detailed explanation page 400-4 for the activity shown. In response to this request, the server 202 can transmit the corresponding hypertext document to the client computer 206 so it can be rendered (e.g., on a web browser). As shown in the example of FIG. 7, there can be a title and brief description 428 and a notes and explanation section 426. The notes and explanation section allow the patient to keep a log and notes of process. The steps bar 430 provide some step-by-step guidance from the educator/administrator, and the share bar 432 enables the patient to share images and text of the progress of the activity with others patients in the community.

Figure 8:
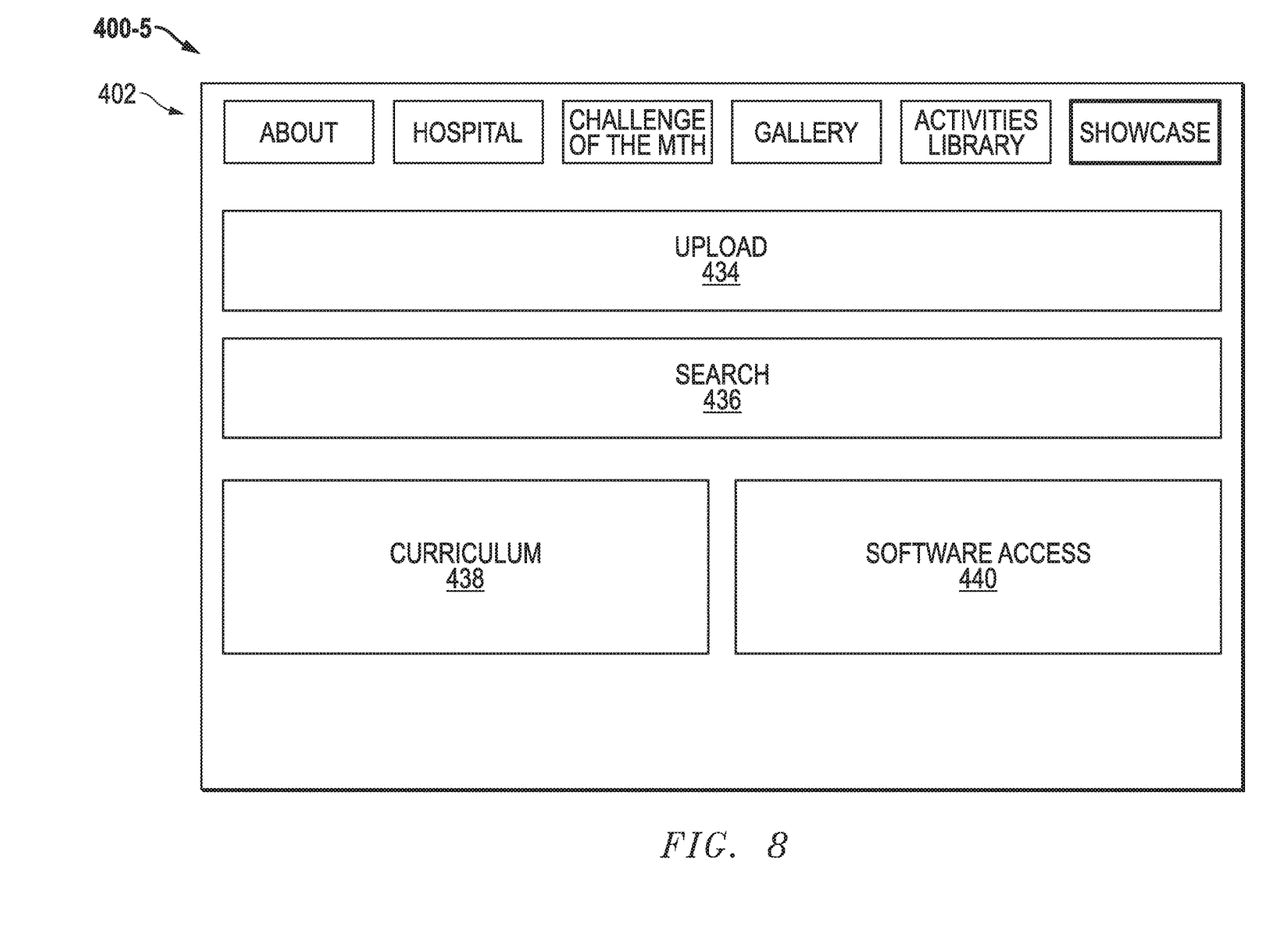

In the example page shown in FIG. 8, there is a difference between page 400-5 and 400-1 to 400-4 in that page 400-5 enables access to dynamic content. As shown in this example, a patient is able to upload content to the online community in bar 434, search the online community in bar 436, and review curriculum in bar 438. More importantly, however, the software access bar 440 can enable the patient to access design software suites or application like LEGO® Digital Designer, INKSCAPE™, or AUTODESK® FUSION™. Typically, due to both license and stability reasons, the applications are launched remotely and accessed through a browser or dedicated application on the client computer 206. The patient can manipulate to software to create design files—which again are typically stored remotely from the client computer 206. Usually, by storing the design files (e.g. CAD files or other vector files) remotely, the server 202 can "push" component design files to the 3D printer located in the activity cart 204 (which can also be request from the software access bar 440).

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Accordingly, it is appropriate that the appended claims be construed broadly and in a manner consistent with the scope of the invention.

The invention claimed is:

1. A method for educating a patient through a collaborative network, the method comprising:
   authenticating the patient with a username and a password, wherein the username and password are registered by way of an authentication number provided through a hospital entry process such that the authentication number ensures the authenticity of the patient and ensures that patient information is gapped to ensure privacy;
   receiving a request by a server from a client computer for entry to a repository for a plurality of educational design activities, wherein each of the plurality of educational design activities includes exemplar design configurations and material lists, and wherein each of the plurality of educational design activities is configured to include photographs and written texts for other patients who have completed the associated educational design activity;
   transmitting a hypertext document to the client computer that includes the plurality of educational design activities, wherein the hypertext document is configured to be displayed through a browsing application on the client computer;
   receiving a request by the server from the client computer for access to a selected education design activity;
   providing access to a design engine for the selected educational design activity;
   storing a design file created by the patient using the design engine;
   transmitting the design file to a shared workstation, wherein the shared workstation includes a vinyl cutting machine; and
   generating vinyl shapes based at least in part on the design file.

2. The method of claim 1, wherein the step of authenticating further comprises creating a secure socket layer (SSL) session.

3. The method of claim 1, wherein the design engine is a computer aided design (CAD) engine is stored remotely from the client computer and accessed through the browsing application on the client computer.

4. The method of claim 1, wherein the browsing application is a web browser.

5. The method of claim 1, wherein the client computer is located on the shared workstation.

6. The method of claim 1, wherein the client computer is a tablet.

7. The method of claim 6, wherein the password is associated with an authentication code the patient.

8. A system for collaboratively educating a patient, the system comprising:
   a server that is adapted to sever a plurality of client computers, wherein each client computer is associated with at least one patient, wherein the server has a computer program product embodied thereon, and wherein the computer program includes:
      computer code for authenticating a first patient from the plurality of patients on a first client computer of the plurality of client computers with a first username and a password, wherein the username and password are registered by way of an authentication number provided through a hospital entry process such that the authentication number ensures the authenticity of the patient and that ensures that patient information is gapped to ensure privacy;
      computer code for receiving a request by the server from first client computer for entry to a repository for a plurality of educational design activities, wherein each of the plurality of educational design activities includes exemplar design configurations and material lists, and wherein each of the plurality of educational design activities is configured to include photographs and written texts for other patients who have completed the associated educational design activity;
      computer code for transmitting a hypertext document to the first client computer that includes the plurality of education design activities, wherein the hypertext document is configured to be displayed through a browsing application on the first client computer;
      computer code for receiving a request by the server from the first client computer for access to a selected education design activity;
      computer code for providing access to a design engine for the selected educational design activity; and
      computer code for storing a design file created by the first patient using the design engine; and
   a shared workstation that is configured to receive control instructions from the server, wherein the workstation includes a 3D printer that is configured to generate components in response to design data supplied by the server, wherein the design data includes the design file.

9. The system of claim 7, wherein the step of authenticating further comprises creating an SSL session.

10. The system of claim 7, wherein the design engine is a CAD engine.

11. The system of claim 9, wherein the CAD engine is stored remotely from the client computer and accessed through the browsing application on the client computer.

12. The system of claim 7, wherein the browsing application is a web browser.

13. The system of claim 7, wherein the client computer is located on the shared workstation.

14. The system of claim 7, wherein the client computer is a tablet or smartphone.

15. The method of claim 6, wherein the password entered by the first patient is associated with an authentication number.

16. A method for educating a patient through a collaborative network, the method comprising:

receiving a request for access by an activity server over a switched packet network to a webpage from a web browser resident on a client computer associated with the patient;

transmitting a first hypertext document to the client computer over the switched packet network, wherein the first hypertext document includes entry boxes for a username and password, and wherein the username and password are associated with an authentication number provided through a hospital entry process such that the authentication number ensures the authenticity of the patient and ensures that patient information is gapped to ensure privacy;

authenticating the patient with the username and the password through the use of an authentication server so as to use an SSL session;

transmitting a second hypertext document to the client computer, wherein the second hypertext document, when rendered on the web browser resident on the client computer, includes a banner with a plurality of selection buttons, wherein a first selection button from the plurality of selection includes permits access a repository for a plurality of education design activities;

receiving a request by the activity server from the client computer for entry to the repository, wherein each of the plurality of educational design activities includes exemplar design configurations and material lists, and wherein each of the plurality of educational design activities is configured to include photographs and written texts for other patients who have completed the associated educational design activity;

receiving a request by the server from the client computer for access to a selected education design activity;

providing access to a CAD engine for the selected educational design activity, wherein the CAD engine operates remotely from the client computer, and wherein the CAD engine is configured to be manipulated through the web browser;

storing a design file created by the patient using the design engine at a location remote from the client computer;

transmitting the design file to a share workstation, wherein the shared workstation includes a 3D printer; and printing a component on the 3D printer based at least in part on the CAD file.

* * * * *